Aug. 6, 1957 E. S. BOERNER Plant Pat. 1,629
ROSE PLANT
Filed Dec. 3, 1956
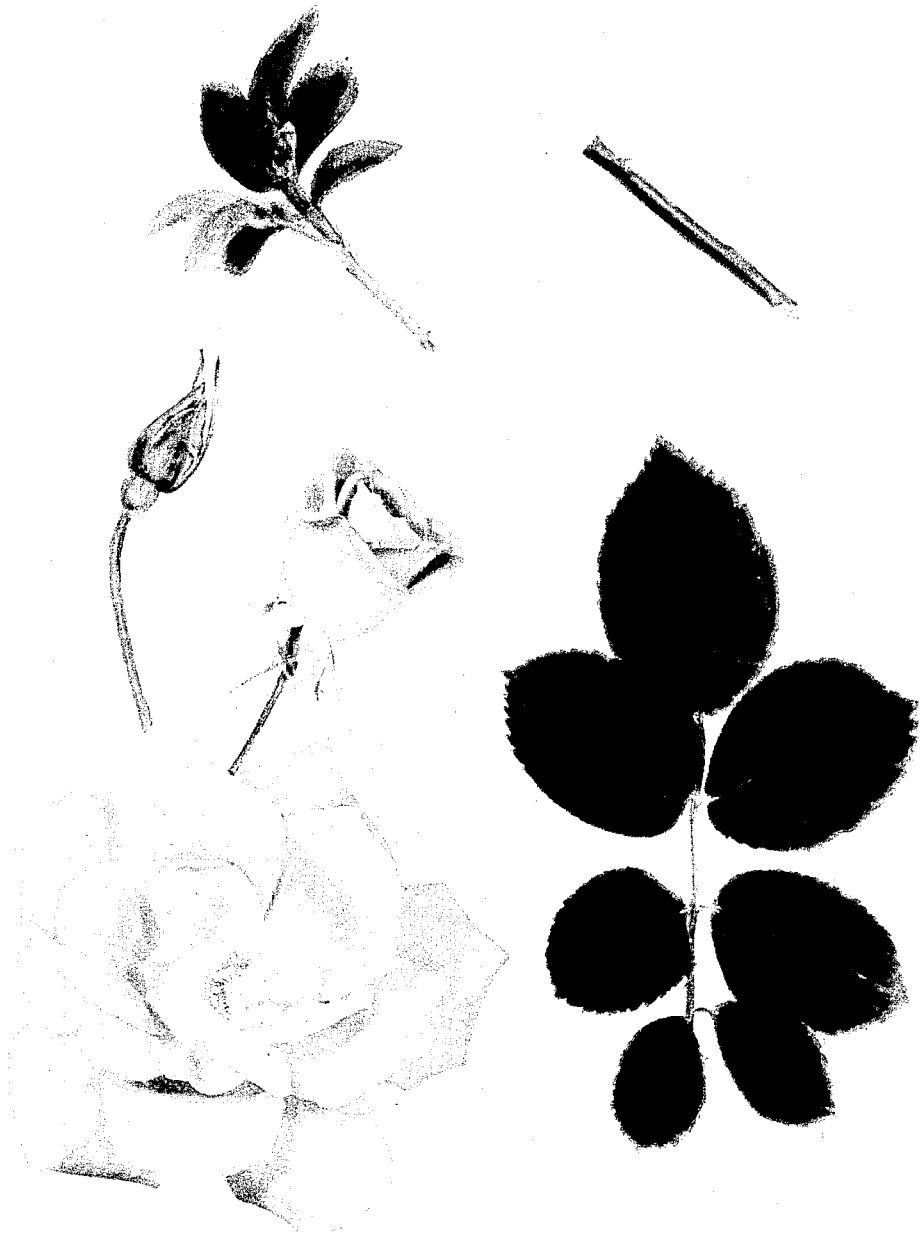
Inventor.
E. S. Boerner
By: Robb & Robb
Attorneys.

United States Patent Office

Plant Pat. 1,629
Patented Aug. 6, 1957

1,629

ROSE PLANT

Eugene S. Boerner, Newark, N. Y., assignor to Jackson & Perkins Company, Newark, N. Y., a corporation of New York Application December 3, 1956, Serial No. 626,070

1 Claim. (Cl. 47—61)

The present invention relates to a new and distinct variety of rose plant of the large-flowered polyantha class, which was originated by me by crossing an unnamed and unpatented seedling derived from a cross of the variety Pinocchio (Plant Patent No. 484) by an unnamed and unpatented red-flowered seedling, with another unnamed and unpatented seedling derived from crossing the variety "Dickson's Red" (Plant Patent No. 376) by an unnamed and unpatented seedling not identified.

The primary objective of this breeding was to produce a new rose variety of the floribunda type which bears red flowers of large size. This objective was fully achieved, along with other improved features, which together, represent a new combination in a rose of this class.

The following characteristics, in particular, differentiate the new variety from its parents, as well as from all other varieties of which I am aware:

(1) Vigorous branching growth and multiple blooming habit;

(2) Needle-like thorns that are hooked downward;

(3) Large, semi-single flowers;

(4) Spectrum Red general color tonality of the flowers, with a distinct ring of Lemon-Yellow color at the base of the petals; and (5) Anthers of Deep Chrome color, with filaments of Coral Red color.

A sexual reproduction of my new variety by budding as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Pinocchio" × an unnamed red seedling.

*Pollen parent.*—An unnamed seedling of "Dickson's Red" × an unnamed and unidentified seedling.

Classification:

*Botanic.*—Large-flowered polyantha.

*Commercial.*—Floribunda.

*Flower*

(Observations made from specimens grown outdoors at Newark, New York, in the early afternoon and in the latter part of July.)

Blooming habit: Recurrent—continuous.

Bud:

*Size.*—Medium.

*Form.*—Pointed; is not affected by wet or hot weather.

*Color.*—When sepals first divide—Pomegranate Purple, Plate 12. When petals begin to unfurl—Spectrum Red, Plate 1. When half-blown: inside of petals—Nopal Red, Plate 1, lightly overcast with Spectrum Red, Plate 1; reverse of petals—Spectrum Red, Plate 1, lightly overcast with Rose Red, Plate 12.

*Sepals.*—Slightly branched; curl back when petals begin to unfurl. Color: inside—Pale Olivine, Plate 32; outside—Light Bice Green, Plate 17.

*Calyx.*—Color—Light Bice Green, Plate 17. Shape—pear. Size—small. Aspect—smooth. Odor when rubbed—none.

*Peduncle.*—Length — medium. Aspect — rough. Strength — erect; slender. Color — Oil Green, Plate 5.

*Opening.*—Opens up well; is not affected by adverse weather conditions.

Bloom:

*Size.*—Medium. Average size when fully expanded—from 4 to 4½ inches.

*Borne.*—In irregular clusters.

*Stems.*—Medium length; normal strength.

*Form (when first open).*—Flat. Permanence—retains its form to the end.

*Petalage.*—Semi-Single (two rows of petals). Number of petals under normal conditions—from 15 to 20.

*Color.*—Center of flower—Scarlet Red, Plate 1, lightly overcast with Rose Red, Plate 12. Outer petals—Rose Red, Plate 12, lightly overcast with Scarlet Red, Plate 1. Base of petals (aiglet)—Lemon Yellow, Plate 4. Inside of petals—Spectrum Red, Plate 1, lightly overcast with Rose Red, Plate 12. Reverse of petals—Rose Red, Plate 12. General tonality from a distance—Spectrum Red, Plate 1.

*Discoloration.*—General tonality at end of first day—Spectrum Red, Plate 1. Second day—Scarlet Red, Plate 1. Third day—Scarlet Red, Plate 1, lightly overcast with Rose Red, Plate 12.

Petals:

*Texture.*—Leathery; is not affected by wet or hot weather.

*Appearance.*—Inside—velvety. Outside—shiny.

*Form.*—Round; slightly notched.

*Arrangement.*—Imbricated (regularly arranged shingle-like).

*Petaloids in center.*—Few; large.

*Persistence.*—Drop off cleanly.

*Fragrance.*—Moderate. Nature—from nutty to spicy.

*Lasting quality.*—On the plant—long. As cut flower—long.

*Genital Organs*

Stamens, anthers: Small; many; regularly arranged around styles. Color—Deep Chrome, Plate 3.

Stamens, filaments (threads): Medium length. Color—Coral Red, Plate 13.

Pollen: Color—Pale Yellow-Orange, Plate 3.

Styles: Loosely separated; uneven length; medium length; thin.

Stigmas: Color—Naples Yellow, Plate 16.

Ovaries: All enclosed in calyx.

Hips: None.

Seeds: None.

*Plant*

Form: Bush

Growth: Vigorous; branching.

Foliage: Compound of 5 to 7 leaflets.

*Size.*—Large.

*Quantity.*—Normal.

*Color.*—New foliage: upper side—Chromium Green, Plate 32, lightly overcast with Oxblood Red, Plate 1, with serrations of Oxblood Red, Plate 1; under side—Oxblood Red, Plate 1, with center of leaf Absinthe Green, Plate 31. Old foliage: upper side—Deep Dull Yellow-Green, Plate 32; under side—Light Elm Green, Plate 17.

*Shape.*—Oval pointed.

*Texture.*—Upper side—leathery. Under side—smooth.

*Ribs and veins.*—Ordinary.

*Edge.*—Serrated (sawtoothed).

*Serration.*—Both double and single; small.

*Leaf stem.*—Color—Parrot Green, Plate 6. Under side—prickly.

*Stipules.*—Medium length; serrated; slightly bearded.

Wood:

*New wood.*—Color—Kildare Green, Plate 31. Bark—smooth.

*Old wood.*—Color—Forest Green, Plate 17. Bark—smooth.

Thorns:

*Thorns.*—Quantity: on main stalks from base—ordinary; on laterals from stalk—ordinary. Form—narrow base; needle-like; medium length; hooked downward. Color (when young)—transparent. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its vigorous branching growth and multiple blooming habit, its needle-like thorns which are hooked downward, its large, semi-single flowers, the distinctive Spectrum Red general color tonality of its flowers which have a distinct ring of Lemon Yellow color at the base of the flower petals, and their anthers of Deep Chrome color, with Coral Red filaments.

No references cited.